United States Patent
Rajaiah et al.

(10) Patent No.: US 9,463,145 B2
(45) Date of Patent: *Oct. 11, 2016

(54) DENTURE ADHESIVE COMPOSITIONS

(71) Applicant: The Procter & Gamble Company, Cincinnati, OH (US)

(72) Inventors: Jayanth Rajaiah, Loveland, OH (US); Robert Scott Leonard, Fairfield, OH (US); Rafael Edmundo Bras, West Chester, OH (US); Franco Medeiros, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/212,034

(22) Filed: Mar. 14, 2014

(65) Prior Publication Data

US 2014/0199659 A1    Jul. 17, 2014

Related U.S. Application Data

(63) Continuation of application No. 13/043,649, filed on Mar. 9, 2011, now Pat. No. 8,735,465.

(60) Provisional application No. 61/312,275, filed on Mar. 10, 2010, provisional application No. 61/362,509, filed on Jul. 8, 2010.

(51) Int. Cl.
*A61C 13/23* (2006.01)
*A61K 6/00* (2006.01)
*A61C 13/225* (2006.01)

(52) U.S. Cl.
CPC ........... *A61K 6/0026* (2013.01); *A61C 13/225* (2013.01)

(58) Field of Classification Search
CPC .... A61K 6/0026; C08L 35/08; A61C 13/225
USPC .......................................... 523/120; 433/180
See application file for complete search history.

(56) References Cited

U.S. PATENT DOCUMENTS

| | | | |
|---|---|---|---|
| 2,496,387 A | 2/1950 | Fink | |
| 3,003,988 A | 10/1961 | Germann et al. | |
| 3,736,274 A | 5/1973 | Schoenholz et al. | |
| 3,865,765 A * | 2/1975 | Drelich et al. | 524/28 |
| 4,108,823 A | 8/1978 | Yoshimura et al. | |
| 4,373,036 A | 2/1983 | Chang et al. | |
| 4,484,894 A | 11/1984 | Masuhara et al. | |
| 4,495,314 A | 1/1985 | Keegan | |
| 4,518,721 A | 5/1985 | Dhabhar et al. | |
| 4,529,748 A | 7/1985 | Wienecke | |
| 4,569,955 A * | 2/1986 | Dhabhar | 523/120 |
| 4,632,880 A | 12/1986 | Lapidus | |
| 4,804,412 A | 2/1989 | Komiyama et al. | |
| 4,880,702 A | 11/1989 | Homan et al. | |
| 4,948,580 A | 8/1990 | Browning | |
| 4,980,391 A | 12/1990 | Kumar et al. | |
| 5,006,571 A | 4/1991 | Kumar | |
| 5,011,868 A | 4/1991 | Keegan | |
| 5,024,701 A * | 6/1991 | Desmarais | 106/35 |
| 5,037,924 A | 8/1991 | Tazi et al. | |
| 5,061,182 A | 10/1991 | Kubo et al. | |
| 5,073,604 A * | 12/1991 | Holeva et al. | 525/327.8 |
| 5,082,913 A | 1/1992 | Tazi et al. | |
| 5,093,387 A | 3/1992 | Schobel et al. | |
| 5,158,825 A | 10/1992 | Altwirth | |
| 5,209,777 A | 5/1993 | Altwirth | |
| 5,239,017 A | 8/1993 | Pelesko et al. | |
| 5,279,884 A | 1/1994 | Kitamura et al. | |
| 5,286,764 A * | 2/1994 | Prosise | 523/120 |
| 5,525,652 A | 6/1996 | Clarke | |
| 5,658,586 A | 8/1997 | Rajaiah et al. | |

(Continued)

FOREIGN PATENT DOCUMENTS

| | | |
|---|---|---|
| DE | 3715100 | 11/1987 |
| GB | 1 492 660 | 11/1997 |
| JP | 55-56611 | 4/1980 |
| JP | 56-68676 | 6/1981 |
| JP | 07-178120 | 7/1985 |

(Continued)

OTHER PUBLICATIONS

Fumiaki Kawano, DDS, PhD, et al, Impact Absorption of Four Processed Soft Denture Liners as Influenced by Accelerated Aging, International Journal of Prosthodontics, vol. 10, No. 1, Jan.-Feb. 1997, pp. 55-60, United States.

(Continued)

*Primary Examiner* — Michael Pepitone

(74) *Attorney, Agent, or Firm* — James E. Oehlenschlager

(57) ABSTRACT

Denture adhesive compositions having good hold and improved taste containing a salt of a copolymer of alkyl vinyl ether-maleic acid or anhydride. Compositions containing from about 25% to about 45%, by weight of the composition, of a salt of a copolymer of alkyl vinyl ether-maleic acid or anhydride containing a cationic salt function containing: i) from about 60% to about 72% cations selected from calcium, strontium, magnesium, or combinations thereof; ii) from 0% to about 10% sodium cations; iii) less than 1% zinc cations; and iv) from about 25% to about 40% of a free acid component; and further containing from about 15% to about 25%, by weight of the composition of a carboxymethyl cellulose having a molecular weight of from about 200,000 to about 1,000,000 daltons; and a carrier. Methods of improving the adhesion of dentures to the oral cavity by applying such compositions to dentures, the oral cavity, or both, and thereafter securing the denture to the ridge or palate of the oral cavity.

16 Claims, No Drawings

(56) References Cited

U.S. PATENT DOCUMENTS

| | | |
|---|---|---|
| 5,696,181 A | 12/1997 | Chang |
| 5,700,478 A | 12/1997 | Biegajski et al. |
| 5,750,591 A * | 5/1998 | Clarke et al. .......... 523/120 |
| 5,753,723 A * | 5/1998 | Chang et al. .......... 523/120 |
| 5,763,554 A | 6/1998 | Prosise et al. |
| 5,877,233 A | 3/1999 | Liang et al. |
| 5,880,172 A | 3/1999 | Rajaiah et al. |
| 5,900,470 A | 5/1999 | Prosie et al. |
| 6,110,989 A | 8/2000 | Clarke et al. |
| 6,149,940 A | 11/2000 | Maggi et al. |
| 6,166,102 A | 12/2000 | Ahn et al. |
| 6,197,331 B1 | 3/2001 | Lerner et al. |
| 6,224,372 B1 | 5/2001 | Ibsen et al. |
| 6,241,972 B1 | 6/2001 | Herms et al. |
| 6,276,937 B1 | 8/2001 | Gasman |
| 6,350,794 B1 | 2/2002 | Borja |
| 6,375,963 B1 | 4/2002 | Repka et al. |
| 6,475,497 B1 | 11/2002 | Rajaiah et al. |
| 6,475,498 B1 | 11/2002 | Rajaiah et al. |
| 6,503,312 B2 | 1/2003 | Altwirth |
| 6,617,374 B1 | 9/2003 | Rajaiah et al. |
| 6,706,781 B2 | 3/2004 | Rajaiah et al. |
| 6,719,995 B2 | 4/2004 | Rajaiah et al. |
| 6,905,672 B2 | 6/2005 | Rajaiah et al. |
| 7,195,484 B1 | 3/2007 | Wagner |
| 7,312,256 B2 | 12/2007 | Borja |
| 7,834,066 B2 | 11/2010 | Rajaiah et al. |
| 8,735,465 B2 * | 5/2014 | Rajaiah et al. .......... 523/120 |
| 2003/0027887 A1 | 2/2003 | Rajaiah et al. |
| 2003/0108488 A1 | 6/2003 | Rajaiah et al. |
| 2003/0108489 A1 | 6/2003 | Rajaiah et al. |
| 2003/0180359 A1 | 9/2003 | Vergnault et al. |
| 2004/0028930 A1 | 2/2004 | Wong et al. |
| 2004/0034120 A1 | 2/2004 | Patel et al. |
| 2004/0101492 A1 | 5/2004 | Dolan et al. |
| 2004/0166068 A1 | 8/2004 | Rajaiah et al. |
| 2005/0228066 A1 | 10/2005 | Wong et al. |
| 2006/0106128 A1 | 5/2006 | Borja |
| 2007/0129460 A1 | 6/2007 | Rajaiah |
| 2007/0134622 A1 | 6/2007 | Rajaiah et al. |
| 2007/0185232 A1 | 8/2007 | Rajaiah |
| 2007/0185233 A1 | 8/2007 | Rajaiah |
| 2007/0185235 A1 | 8/2007 | Rajaiah et al. |
| 2007/0185236 A1 | 8/2007 | Rajaiah |
| 2007/0185237 A1 | 8/2007 | Rajaiah |
| 2007/0196787 A1 | 8/2007 | Smetana et al. |
| 2009/0238776 A1 | 9/2009 | Baig et al. |
| 2009/0239972 A1 | 9/2009 | Rajaiah et al. |
| 2010/0317763 A1 | 12/2010 | Rajaiah et al. |
| 2011/0094415 A1 | 4/2011 | Rajaiah et al. |

FOREIGN PATENT DOCUMENTS

| | | |
|---|---|---|
| JP | 61-21511 | 2/1986 |
| JP | 63-115805 | 5/1988 |
| JP | 03-090145 | 4/1991 |
| JP | 2001-212160 | 8/2001 |
| JP | 2002-095681 | 4/2002 |
| JP | 2004-141553 | 5/2004 |
| WO | WO9210987 | 7/1992 |
| WO | WO9314737 | 8/1993 |
| WO | WO 96/25910 | 8/1996 |
| WO | WO 97/03641 | 2/1997 |
| WO | WO 97/31614 | 9/1997 |
| WO | WO 01/15657 A1 | 3/2001 |
| WO | WO 01/21093 A1 | 3/2001 |
| WO | WO 01/41710 A | 6/2001 |
| WO | WO 01/41711 A1 | 6/2001 |
| WO | WO 01/51009 A1 | 7/2001 |
| WO | WO 02/30317 A | 4/2002 |
| WO | WO 2004/058195 A1 | 7/2004 |
| WO | WO 2004/108003 | 12/2004 |
| WO | WO 2005/081935 A2 | 9/2005 |
| WO | WO 2007/012859 A2 | 2/2007 |
| WO | WO 2007/056605 A1 | 5/2007 |
| WO | WO 2007/056610 A1 | 5/2007 |
| WO | WO2008112419 | 9/2008 |

OTHER PUBLICATIONS

International Search Report for PCT/US2009/045887 dated Feb. 16, 2011.
Norcliff Thayer et al.: "Polymer mixtures as adhesive for denture", Chemical Abstracts Service, May, 20, 1998, XP 002613948 abstract.
PCT International Search Report dated May 3, 2008.
PCT International Search Report dated Sep. 11, 2006.
PCT International Search Report dated Apr. 25, 2007.
Pct International Serach Report dated Jun. 2, 2009.
Seltzer, R. Self-Adhesive Polymeric Coatings Have Nonstick Surfaces, Chemical and Engineering News, 63, No. 41, Oct. 14, 1985, p. 44-45, United States.

* cited by examiner

DENTURE ADHESIVE COMPOSITIONS

This application is a continuation of U.S. application Ser. No. 13/043,649, filed Mar. 9, 2011, which is now U.S. Pat. No. 8,735,465, issued 27 May 2014, claims the benefit of U.S. Provisional Application No. 61/362,509, filed Jul. 8, 2010, and U.S. Provisional Application No. 61/312,275, filed Mar. 10, 2010, all of which are incorporated herein by reference.

FIELD OF THE INVENTION

The present compositions relate to denture adhesives comprising salts of AVE/MA polymers.

BACKGROUND OF THE INVENTION

Ordinary removable dentures, dental plates and the like, comprise teeth mounted in a suitable plate or base. Denture stabilizers, including denture adhesives, are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used singly, in combination, and in combination with various adhesives and other materials in an attempt to lessen certain deficiencies. These deficiencies include inadequate holding power and messiness and difficulty of removing the residual adhesive from the mouth and dentures. Also, food may become trapped between the denture and the oral cavity of the wearer. Additionally, certain components may present a less than desirable taste to the wearer.

Alkyl vinyl ether-maleic copolymers and salts thereof are known in the art for use in denture adhesive compositions. Such disclosures include: U.S. Pat. No. 3,003,988 to Germann et al., issued Oct. 10, 1961; U.S. Pat. No. 4,980,391 to Kumar et al., issued Dec. 25, 1990; U.S. Pat. No. 5,073,604 to Holeva et al., issued Dec. 17, 1991; U.S. Pat. No. 5,900,470, Prosise et al., issued May 4, 1999; U.S. Pat. No. 5,037,924, Tazi et al, issued Aug. 6, 1991; U.S. Pat. No. 5,082,913, Tazi et al., issued Jan. 21, 1992; and U.S. Pat. No. 5,525,652 to Clarke, issued Jun. 11, 1996. In addition strip or insert denture adhesives are also known. Despite the above-noted technologies, as well as many others, a need still exists for denture stabilizing compositions providing good hold and improved taste.

In accordance with the present invention, good hold and improved taste characteristics may be obtained by using denture adhesive compositions comprising alkyl vinyl ether-maleic acid copolymers comprising combinations of magnesium, strontium, and calcium salts together with specific levels of free acid.

SUMMARY OF THE INVENTION

The present invention relates to a denture adhesive composition comprising a salt of a copolymer of alkyl vinyl ether-maleic acid or anhydride, wherein said adhesive composition comprises: from about 25% to about 45%, by weight of the composition, of a salt of a copolymer of alkyl vinyl ether-maleic acid or anhydride containing a cationic salt function comprising: from about 60% to about 72% cations selected from calcium, strontium, magnesium, or combinations thereof; from 0% to about 10% sodium cations; less than 1% zinc cations; and from about 25% to about 40% of a free acid component; wherein the composition further comprises from about 15% to about 25%, by weight of the composition of a carboxymethyl cellulose having a molecular weight of from about 200,000 to about 1,000,000 daltons; and a carrier.

The present invention further relates to a denture adhesive composition comprising a salt of a copolymer of alkyl vinyl ether-maleic acid or anhydride, wherein said adhesive composition consists essentially of: from about 25% to about 45%, by weight of the composition, of a salt of a copolymer of alkyl vinyl ether-maleic acid or anhydride containing a cationic salt function consisting essentially of: i) from about 60% to about 70% calcium cations; ii) from 0% to about 5% sodium cations; iii) substantially free of zinc cations; and iv) from about 25% to about 35% of a free acid component; and from about 15% to about 25%, by weight of the composition, of a carboxymethyl cellulose having a molecular weight of from about 500,000 to about 900,000; and a carrier comprising a water-insoluble liquid, gel, thermoplastic solid, or combinations thereof.

The present invention further relates to such compositions wherein the cationic salt function is substantially free of zinc cations.

The present invention further relates to the above compositions wherein the cationic salt function consists essentially of calcium cations and from about 25% to about 35% of the free acid component.

The present invention further relates to the above compositions wherein the cationic salt function consists essentially of from about 65% to about 70% calcium cations, from about 0% to about 5% sodium cations and from about 28% to about 32% of the free acid component. The present invention further relates to the above compositions wherein the adhesive composition comprises from about 15% to about 25%, by weight of the composition, of the carboxymethylcellulose.

The present invention further relates to the above compositions wherein the carboxymethylcellulose has a molecular weight of from about 600,000 to about 800,000.

The present invention further relates to the above compositions wherein the salt of a copolymer of alkyl vinyl ether-maleic acid or anhydride has a molecular weight greater than 1,250,000.

The present invention further relates to the above compositions wherein the salt of a copolymer of alkyl vinyl ether-maleic acid or anhydride has a specific viscosity of from about 2.5 to about 3.8 when measured as a 1% in methyl ethyl ketone solution at 25° C.

The present invention further relates to the above compositions further comprising one or more ingredients selected from the group consisting of additional adhesive components, plasticizers, colorants, preservatives, thickeners, vehicles, flavors, fragrances, sensates, and mixtures thereof.

The present invention further relates to the above compositions wherein the cationic salt function consists essentially of from about 65% to about 70% calcium cations and from about 28% to about 32% of the free acid component.

The present invention further relates to the above compositions wherein the adhesive composition comprises from about 15% to about 25%, by weight of the composition, of carboxymethylcellulose having a molecular weight of from about 600,000 to about 800,000.

The present invention further relates to the above compositions wherein the salt of a copolymer of alkyl vinyl ether-maleic acid or anhydride has a molecular weight greater than 1,250,000.

The present invention further relates to the above compositions wherein the salt of a copolymer of alkyl vinyl ether-maleic acid or anhydride has a specific viscosity of from about 2.5 to about 3.8 when measured as a 1% in methyl ethyl ketone solution at 25° C.

The present invention further relates to the above compositions further comprising at least one non-adhesive self-supporting layer.

The present invention further relates to the above compositions wherein the carrier comprises microcrystalline wax.

The present invention further relates to the above compositions wherein the composition is substantially free of magnesium.

The present invention further relates to the above compositions wherein the composition is substantially free of sodium.

The present invention further relates to the above compositions wherein the composition is substantially free of strontium.

The present invention further relates to a method of improving the adhesion of dentures to the oral cavity by applying any one of the above compositions to dentures, the oral cavity, or both, and thereafter securing the denture to the ridge or palate of the oral cavity.

DETAILED DESCRIPTION OF THE INVENTION

The denture adhesive compositions of the present invention comprise carboxymethylcellulose in combination with the magnesium, strontium, and/or calcium salts of an alkyl vinyl ether-maleic copolymer with specific free acid levels, optionally comprising from 0% to about 10% of sodium cations; and substantially free of zinc cations.

The adhesive compositions may be in the form of an article, powder, cream, paste, liquid, aerosol, and/or wafer. Powder forms may be sprinkled on a dental prosthesis, moistened and then inserted into the oral cavity. The compositions may also be combined with various conventional delivery vehicles to form liquids or pastes which can be applied to a dental prosthesis and inserted into the oral cavity. These compositions can optionally comprise at least one non-adhesive self-supporting layer. Denture adhesive compositions with a self-supporting layer may be thoroughly moistened and applied to dentures. A detailed description of essential and optional components of the present invention is given below.

Definitions

The term "safe and effective adhesive amounts" as used herein means an amount sufficient to provide adherence to the oral cavity and/or adherence of a dental prosthesis to the palate and ridge of the oral cavity, without toxicity to the user, damage to oral tissue, and alteration of the denture material.

The term "AVE/MA" as used herein refers to alkyl vinyl ether-maleic acid copolymer. The term "mixed polymer salts" or "mixed salts", as used herein, refers to salts of AVE/MA where at least 2 different cations are mixed on the same polymer with each other or with other ester functions.

The term "free acid" ("FA") component as used herein refers either to the unreacted carboxyl groups (—COOH) of AVE/MA.

The percentages used herein to describe the salt function of the copolymers are defined as the stoichiometric percent of the total initial carboxyl groups reacted on the polymer. All other percentages used herein are by weight unless otherwise indicated.

Polymer

The alkyl vinyl ether-maleic acid ("AVE/MA") copolymer comprises the repeated structural unit:

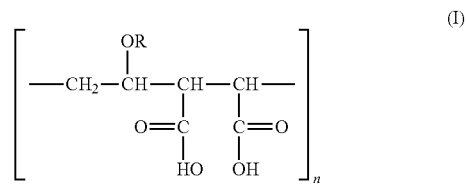

wherein R represents an alkyl radical, in some embodiments a $C_1$ to $C_5$ alkyl radical, and n is an integer greater than one representing the number of repeated occurrences of the structural unit in a molecule of the polymer.

The present denture adhesive compositions comprise salts or mixed salts of an AVE/MA copolymer wherein the salt contains a cationic salt function. The cationic salt function comprises (alternatively consisting essentially of, alternatively consisting of) from about 60% to about 72% of magnesium, strontium, and/or calcium cations, from 0% to about 10% of sodium cations; less than 1%, (alternatively substantially free), of zinc cations; and from about 25% to about 40% free acid component.

The AVE/MA copolymers have a range of specific viscosities. For example, the specific viscosity may be at least 2.0, alternatively 2.5 or higher, alternatively from about 2.5 to about 5, when measured as a 1% weight/volume solution of the starting anhydride or acid of the copolymer, in methyl ethyl ketone at 25° C. In one embodiment, the salt of a copolymer of alkyl vinyl ether-maleic acid or anhydride has a specific viscosity of from about 2.5 to about 3.8 when measured as a 1% in methyl ethyl ketone solution at 25° C.

The AVE/MA copolymers have a molecular weight of at least about 1,250,000 daltons. In some embodiments, the molecular weight is from about 1,500,000 to about 3,000,000, alternatively from about 1,700,000 to about 2,100,000 or from about 1,800,000 to about 2,000,000 daltons.

AVE/MA copolymers commercially available and useful herein include GANTREZ AN169 or GANTREZ 179, available from International Specialty Products, having a typical molecular weight of about 1,980,000 and 2,400,000 respectively, per their brochure materials. Another suitable polymer commercially available is AN169 BF, alson from International Specialty Products.

The AVE/MA copolymers are reacted to form a salt containing a cationic salt function. The cationic salt function comprises from about 60% to about 72% of cations selected from calcium, strontium, magnesium and combinations thereof. In some embodiments, the cationic salt function comprises from about 60% to about 70%, alternatively from about 61% to about 69%, alternatively from about 62% to about 68%, alternatively from about 63% to about 67%, of cations selected from calcium, strontium, magnesium and combinations thereof. In some embodiments, the level of magnesium cations in the cationic salt function may be any combination of the ranges from about 1%, 5%, 10%, 15%, 20%, 25%, 30%, 35%, or 40% to about 20%, 25%, 30%, 35%, 40%, 45%, 50%, 55%, 60%, 61%, 62%, 63%, 64%, 65%, 66%. 67%, 68%, 69% or 70%, of the initial carboxyl groups reacted. In some embodiments, the level of strontium cations in the cationic salt function may be any range combination from about 1%, 5%, 10%, 15%, 20%, 25%, 30%, 35%, or 40% to about 20%, 25%, 30%, 35%, 40%, 45%, 50%, 55%, 60%, 61%, 62%, 63%, 64%, 65%, 66%. 67%, 68%, 69% or 70%, of the initial carboxyl groups reacted. In some embodiments, the level of calcium cations in the cationic salt function may be any combination of the ranges from about 1%, 5%, 10%, 15%, 20%, 25%, 30%, 35%, or 40% to about 20%, 25%, 30%, 35%, 40%, 45%, 50%, 55%, 60%, 61%, 62%, 63%, 64%, 65%, 66%. 67%, 68%, 69% or 70%, of the initial carboxyl groups reacted.

In some embodiments, the cationic salt function may comprise from 0% to about 10%, alternatively from 0% to about 5%, alternatively from about 1% to about 4%; from about 1% to about 3%, or from about 0.5% to about 2% sodium cations. In some embodiments, the cationic salt function may be substantially free of iron, manganese, zinc, copper, sodium, potassium, zirconium, strontium, magnesium, and/or aluminum. In some embodiments, the cationic salt function is substantially free of zinc cations. Without being limited by theory, by limiting the amount of zinc (and other metal) cations in the cationic salt function, the overall taste of the product can be improved. Zinc is known to have an unpleasant taste (see, for example U.S. Pat. No. 6,169, 118) and it therefore may be desirable to formulate a composition that is overall substantially free of zinc. The phrase "substantially free of" means less than 0.0001%, preferably less than 0.001%, more preferably less than 0.01%, and still more preferably less than 0.1%.

In some embodiments, the cationic salt function contains from about 25% to about 40% free acid component. In other embodiments, the free acid component may be any combination of the ranges from about 25%, 30%, 31%, 32%, 33%, 34%, 35%, 36%, 37%, 38%, or 39%, to about 30%, 31%, 32%, 33%, 34%, 35%, 36%, 37%, 38%, 39%, or 40%. Without being limited by theory, the amount of free acid component is relevant in that greater amounts of free acid may give more sites to provide adhesion to wet mucoadhesive surfaces. Furthermore, the amount of free acid is also believed to be useful in optimizing the interaction with a coadhesive such as carboxymethylcellulose. Yet too much free acid may reduce metal cross-linking, and/or increase solubility of the polymer salt, consequently reducing cohesion. Therefore, the amount of free acid component is important to achieving the good adhesiveness of the present compositions, especially with compositions comprising a coadhesive like carboxymethylcellulose.

The alkyl vinyl ether maleic anhydride copolymers are obtained by co-polymerizing an alkyl vinyl ether monomer, such as methyl vinyl ether, ethyl vinyl ether, divinyl ether, propyl vinyl ether and isobutyl vinyl ether, with maleic anhydride to yield the corresponding alkyl vinyl ether-maleic anhydride copolymer which is readily hydrolyzable to the acid copolymer. Suitable copolymers may be prepared by well-known methods of the prior art, for example U.S. Pat. No. 2,782,182, and U.S. Pat. No. 2,047,398. Both anhydride and acid forms are also available from commercial suppliers. For example, the GAF Corporation, Wayne, N.J. provides both the polymeric free acid form (I) and the corresponding anhydride form under its "GANTREZ" trademark as the "GANTREZ S Series" and "GANTREZ AN Series", respectively. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

The salt form of the subject polymers may be prepared by the interaction of the AVE/M anhydride or acid copolymer with at least one cationic salt function, such as magnesium, strontium, or calcium, and optionally sodium, compounds having a functional group typical of reactants of a carboxylic acid, such as, for example, the hydroxide, oxide, acetate, halide, lactate, etc. in an aqueous medium. In one embodiment, the magnesium oxide, strontium hydroxide, strontium carbonate, and/or calcium hydroxide are utilized.

Ions that form toxic, irritating or contaminating by-products should be avoided, or special precautions and treatment provided to assure the removal and absence of such by-products from the polymeric salt end-product. The particular compound used should be substantially pure to assure obtaining a substantially pure, polymeric salt end-product.

An aqueous dispersion of particulate metal compounds may be combined with the powder polymer, in the form of a slurry, in an amount sufficient to provide the desired cationic content desired in the end-product. This is done at ambient temperature and then slowly heated to 70°-95° C. with continuous vigorous mixing so as to prevent localized precipitation of the cationic polymeric salt; mixing is continued to ensure that all the salt forming compound is reacted with the copolymer.

Alternatively, the polymer may be hydrolyzed and neutralized in an aqueous mixture or slurry of one or more divalent and/or monovalent metal bases by heating the polymer/base mixture to a temperature ranging from about 45° C. to about 100° C. In either of the above processes, the resulting slurry or solution may be transferred to shallow stainless steel drying trays and placed in a forced air mechanical convection oven at 60-70° C. for a time sufficient to evaporate the reaction medium (water) and remove water from the polymer (about 18-24 hours). Alternatively, the resulting slurry or solution can be drum-dried at 100° to 200° C. with hot steam to evaporate the water content and recover the polymer in the flake form. After drying, the polymer forms brittle flakes which can easily be peeled off from the trays or drum surface and ground to a fine powder as desired to provide satisfactory denture stabilizing properties. Methods of making these salts of AVE/MA polymers are further disclosed in U.S. Pat. No. 5,073,604, Holeva et al., issued Dec. 17, 1991 and U.S. Pat. No. 5,872,161, Liang et al., issued Feb. 16, 1999; U.S. Pat. No. 5,830,933, Synodis et al., issued Nov. 3, 1998.

The salt polymers have good taste and/or adhesive qualities when contacted with water or saliva such that they are extremely useful as denture adhesive materials in denture compositions. The compositions of the present invention comprise a safe and effective adhesive amounts of the salt polymers, in some embodiments at least 10, 20, 30, or 40 percent by weight, as the sole adhesive component or as a co-adhesive in joint usage with other adhesive components.

Carboxymethylcellulose

The denture adhesive compositions herein further contain from about 10% to about 30%, optionally from about 15% to about 25%, or from about 17% to about 20%, by weight of the adhesive composition, of carboxymethylcellulose. In one embodiment, the carboxymethylcellulose is sodium carboxymethylcellulose. Carboxymethylcellulose materials useful herein include those having a molecular weight of at least 200,000 daltons. In some embodiments, the carboxymethylcellulose has a molecular weight of from about 200,000 to about 1,000,000, alternatively from about 500,000 to 900,000, or from about 600,000 to about 800,000 daltons. Examples of commercially available carboxymethylcelluloses useful herein include the 7H series of carboxymethylcelluloses available from Aqualon having a typical molecular weight of about 700,000 daltons per their brochure materials. Other examples of commercial available carboxymethylcellulose include 7H3SX8F from Aqualon/Hercules and CEKOL 30,000P from C.P. Kelco/Noviant/Huber.

Carrier

The present denture adhesive compositions comprise from about 2% to about 80% and in another embodiment from about 30% to about 70%, of a carrier such as a water-insoluble liquid, gel, thermoplastic solid, or combinations thereof.

In general, water-insoluble blends of mineral oil and petrolatum may be used to make the composition into a suspension. This suspension of solid-particles in a liquid/gel vehicle/carrier is also referred to as a denture adhesive cream or paste. In some embodiments, the present composition comprises a safe and effective amount of a water insoluble component (wic). In one embodiment this component is present by weight of the composition at an amount from about 2, 5, 10, 20, 25, 30, 35% to about 45, 50, 60, 70, 90%, or any combination thereof. In additional embodiments the water insoluble component is present at an amount from about 20% to about 70%, from about 25% to about 60%, or from about 35% to about 60% by weight of the composition. In yet another embodiment the water insoluble component is substantially non-swellable in water. In some embodiments, the non-swellable water insoluble component swells less than about 10%, 5%, 2%, or 1% in water.

In one embodiment, the water insoluble component comprises a liquid, gel, or mixtures thereof. In one embodiment, the water insoluble component is selected from the group consisting of: natural wax, synthetic wax, petrolatum, polyvinyl acetate, natural oils, synthetic oils, fats, silicone, silicone derivatives, dimethicone, silicone resins, hydrocarbons, hydrocarbon derivatives, essential oils, caprilic/capric triglycerides, polybutene, oleic acid, stearic acid, and combinations thereof. In a further embodiment, the water insoluble component comprises petrolatum, polyvinyl acetate, natural oils, synthetic oils, fats, silicone, silicone derivatives, dimethicone, silicone resins, hydrocarbons, hydrocarbon derivatives, polybutene, oleic acid, stearic acid, essential oils, or combinations thereof.

Examples of natural oils include, but are not limited to, vegetable oils (ex. corn oil), soy bean oils, cottonseed oils, palm oils, coconut oils, mineral oils, animal oils (ex. fish oils), etc. Examples of synthetic oils include, but are not limited to, silicone oils, etc. In one embodiment, the water insoluble component comprises a natural oil. In an additional embodiment, the water insoluble component is substantially free of petrolatum. In another embodiment, the water insoluble component further comprises petrolatum. In other embodiments, the water insoluble component may comprise mineral jelly, for example, mineral jellies numbers 4, 5, 10, 15, or 20 from Calumet Specialty Products.

In a further embodiment, the natural oil comprises mineral oil. In one embodiment, mineral oil is present in the composition at an amount from about 30% to about 50% and in another embodiment, from about 35% to about 45%. In some embodiments, the mineral oil may be white, light, or technical. Light mineral oil may be, for example, Drakeol 5, 10, 13, or 15. White mineral oil may be, for example, Drakeol 19, 21, 34, 35, or 600.

In some embodiments, the water insoluble component comprises a wax. Waxes are generally made up of various substances including hydrocarbons (normal or branched alkanes and alkenes), ketones, diketones, primary and secondary alcohols, aldehydes, sterol esters, alkanoic acids, terpenes (squalene) and monoesters (wax esters). Different types of waxes include animal and insect waxes (beeswax, Chinese wax, shellac wax, spermaceti, lanolin), vegetable waxes (bayberry wax, candelilla wax, carnauba wax, castor wax, esparto wax, Japan wax, jojoba oil, ouricury wax, rice bran wax), mineral waxes (cresin waxes, montan wax, ozocerite, peat waxes), petroleum waxes (paraffin wax or microcrystalline wax), and synthetic waxes (polyethylene waxes, Fischer-Tropsch waxes, chemically modified waxes, substituted amide waxes, polymerized α-olefins).

In one embodiment the water insoluble component comprises a natural or synthetic wax. In a further embodiment, the natural wax is selected from the group consisting of: animal wax, vegetable wax, mineral wax, and combinations thereof. In another embodiment, the animal wax includes beeswax, lanolin, shellac wax, Chinese wax, and combinations thereof. In another embodiment, the vegetable waxes include carnauba, candelilla, bayberry, sugar cane, and combinations thereof; and mineral waxes include fossil or earth waxes (ozocerite, ceresin, montan), and petroleum waxes such as paraffin and microcrystalline wax, and combinations thereof. In one embodiment the waxes herein are natural waxes selected from the group consisting of beeswax, candelilla, candela, carnauba, paraffin, and combinations thereof. In varying embodiments, wax can be present in an amount from about 1, 2, 5, 8% to about 5, 10, 20, 30%, or any combination thereof.

In another embodiment, the natural wax comprises paraffin wax. A paraffin wax useful herein generally can have a melting point range of from about 65° C. to about 80° C. and, in another embodiment, from about 70° C. to about 75° C. In another embodiment, a microcrystalline wax useful herein can have a melting point of from about 65° C. to about 90° C., and, in another embodiment from about 80° C. to about 90° C. In one embodiment, a beeswax useful herein can have a melting point of from about 62° C. to about 65° C. and a flash point of 242° C. In another embodiment, a candelilla wax useful herein can have a melting point of from about 68° C. to about 72° C. In an additional embodiment, a carnauba wax useful herein can have a melting point of from about 83° C. to about 86° C. In one embodiment, a Fischer-Tropsch wax useful herein can have a melting point of about 95° C. to about 120° C. Synthetic grades of beeswax, candelilla, and carnauba waxes are also available with similar properties as the natural grades.

In one embodiment, the water insoluble component comprises petrolatum. According to Hawley's Condensed Chemical Dictionary 13th Edition, John Wiley & Sons, 1997, petrolatum is a "mixture of hydrocarbons derived by distillation of paraffin-base petroleum fractions"; and according to The United States Pharmacopia 2005, petrolatum is a "purified mixture of semisolid hydrocarbons obtained from petroleum". This is also referred to as "natural petrolatum". Petrolatum is stated to have a melting range between 38° C. and 60° C. according to The United States Pharmacopia 2005, and 38-54 C according to The Merck Index, 10th Edition, 1983. Petrolatums are available in a variety of grades with the "Cone Penetration Values" ranging from 180 to about 245 measured using ASTM D-937 according to the Sonneborn Inc product brochure.

In one embodiment, the water insoluble component has a melting point greater than about 60° C. In some embodiments, the water insoluble thermoplastic component has a melting point from about 35° C., 40° C., 45° C., 50° C., 55° C., 60° C., 65° C., 70° C., 75° C., 80° C., 85° C., 90° C., 95° C., 100° C., to about 110° C., 120° C., 150° C., 175° C., 200° C. and/or any combination thereof to form a range, starting point, and/or end point. In another embodiment, the composition is substantially free of a water insoluble thermoplastic component with a melting point above about 75° C.

In some embodiments, the carrier comprises microcrystalline wax. The microcrystalline wax may be refined and/or substantially pure. In an additional embodiment, petrolatum does not contribute the microcrystalline wax. The "Encyclopedia of Polymer Science and Engineering", $2^{nd}$ Edition, Vol. 17, page 788, hereby incorporated by reference, states that the molecular weight of microcrystalline wax ranges from 450 to 800. The "Kirk-Othmer Encyclopedia of Chemical Technology", $5^{th}$ Edition, vol. 26, page 216, hereby incorporated by reference, states that microcrystalline wax has the following typical properties: flash point, closed cup, 260° C.; viscosity at 98.9° C., 10.2-25 $mm^2/s$; melting range, 60° C.-93° C.; refractive index at 98.9° C., 1.435 to 1.445; average molecular weight, 600 to 800; carbon atom per molecule, 30 to 75; and ductibility/crystallinity of solid wax, ductile-plastic to tough-brittle, and in one embodiment, the viscosity index improver has these particular properties.

In another embodiment, the microcrystalline wax has a melting point ranging from about 50° C. to about 100° C. In further embodiments, the microcrystalline wax has a melting point ranging from about 50° C., 55° C., 60° C., 65° C., 70° C. to about 70° C., 75° C., 80° C., 85° C., 90° C., 95° C., 100° C., or any combination thereof. In one particular embodiment, the microcrystalline wax has a melting point ranging from about 75° C. to about 85° C.

In another embodiment the microcrystalline wax is manufactured by Crompton, Sonneborn (Witco) and referred to and sold under the trademark Mutiwax®W-835. This wax has a melting point ranging from about 73.9° C. to about 79.4° C. (measured using ASTM D-127), has a penetration at 25° C. of from about 60 to about 80 (measured using ASTM D-1321), has a kinematic viscosity at 98.9° C. of from about 75 to about 90 saybolt universal seconds (measured using ASTM D-2161), has a flash point, COC (Cleveland open cup), of at least about 246° C. (measured using ASTM D-92), and has a congealing point from about 68° C. to about 77° C. (measured using ASTM D-938).

In another embodiment the microcrystalline wax is manufactured by Crompton, Sonneborn (Witco) and referred to and sold under the trademark Mutiwax®180W. This wax has a melting point ranging from about 79° C. to about 87° C. (measured using ASTM D-127), has a penetration at 25° C. of from about 15 to about 22 (measured using ASTM D-1321), has a kinematic viscosity at 98.9° C. of at least about 75 saybolt universal seconds (measured using ASTM D-2161), has a flash point, COC (Cleveland open cup), of at least about 277° C. (measured using ASTM D-92), and has a congealing point from about 75° C. to about 82° C. (measured using ASTM D-938).

In another embodiment the microcrystalline wax is manufactured by Crompton, Sonneborn (Witco) and referred to and sold under the trademark Mutiwax®W445. This wax has a melting point ranging from about 77° C. to about 82° C. (measured using ASTM D-127), has a penetration at 25° C. of from about 25 to about 35 (measured using ASTM D-1321), has a kinematic viscosity at 98.9° C. of from about 75 to about 90 saybolt universal seconds (measured using ASTM D-2161), has a flash point, COC (Cleveland open cup), of at least about 277° C. (measured using ASTM D-92), and has a congealing point from about 72° C. to about 77° C. (measured using ASTM D-938).

While microcrystalline wax and paraffin wax are both petroleum waxes, there are specific differences between them. Microcrystalline wax is a refined mixture of solid, saturated aliphatic hydrocarbons produced by de-oiling certain fractions from the petroleum refining process. In contrast to the more familiar paraffin wax which contains mostly unbranched alkanes, microcrystalline wax contains a higher percentage of isoparaffinic (branched) hydrocarbons and naphthenic hydrocarbons. It is characterized by the fineness of its crystals in contrast to the larger crystal of paraffin wax. It consists of high molecular weight saturated aliphatic hydrocarbons. It is generally darker, more viscous, denser, tackier and more elastic than paraffin waxes, and has a higher molecular weight and melting point. The elastic and adhesive characteristics of microcrystalline waxes are related to the non-straight chain components which they contain. Typical microcrystalline wax crystal structure is small and thin, making them more flexible than paraffin wax.

According to the "Encyclopedia of Polymer Science and Engineering" Volume 17 page 788, 1989 John Wiley & Sons): The molecular weights of paraffin waxes range from about 280 to 560 (C20 to C40); the molecular weights of microcrystalline wax range from 450 to 800 (C35 to C60). The amount of n-alkanes in paraffin wax usually exceeds 75% and can be as high as 100%; microcrystalline waxes are composed predominantly of iso-paraffinic and napthenic saturated hydrocarbons along with some n-alkanes.

According to Kirk-Othmer Encyclopedia of Chemical Technology, John Wiley & Sons, 2005: Paraffin Waxes have a number average molecular weight of 350-420 and carbons per molecule of 20-36; and Microcrystalline waxes have a number average molecular weight of 600-800 and carbons per molecule of 30-75. Paraffin wax is macrocrystalline, brittle, and is composed of 40-90% normal alkanes, with the remainder C18-C36 isoalkanes and cycloalkanes. A paraffin wax is a petroleum wax consisting principally of normal alkanes. Microcrystalline wax is a petroleum wax containing substantial proportions of branched and cyclic saturated hydrocarbons, in addition to normal alkanes. A classification system based on the refractive index of the wax and its congealing point as determined by ASTM D-938 has been developed. Paraffin waxes have a refractive index at 98.9 C of 1.430-1.433; and microcrystalline waxes have a refractive index at 98.9 C of 1.435-1.445. Paraffin waxes are friable to crystalline; microcrystalline waxes are ductile-plastic to tough-brittle. Paraffin wax has little affinity for oil; microcrystalline wax has great affinity for oil. Unlike paraffin wax, oil is held tightly in the crystal lattice of the microcrystalline wax, and does not migrate to the surface. Paraffin wax is stated to have a melting point of about 47-65° C., according to Hawley's Condensed Chemical Dictionary $13^{th}$ Edition, John Wiley & Sons, 1997, and 46-68° C., according to Kirk-Othmer Encyclopedia of Chemical Technology, John Woley & Sons, 2005. Microcrystalline wax is stated to have a melting point of about 63-88° C., according to Hawley's Condensed Chemical Dictionary $13^{th}$ Edition, John Wiley & Sons, and 60-93° C., according to according to Kirk-Othmer Encyclopedia of Chemical Technology, John Wiley & Sons, 2005.

In some embodiments, the water insoluble thermoplastic and/or viscosity index improver used in the present invention have a Penetration Value from about 5, 10, 15, 20, 25, 30, 35, 40, 45, 50, 55, 60 to about, 25, 30, 35, 40, 45, 50, 55, 60, 65, 70, 75, 80, 85, 90, 95, 100, 110, 120, 250, in any combination of numbers to form ranges.

In some embodiments, the water insoluble thermoplastic component and/or viscosity index improver such as microcrystalline wax has an average molecular weight higher than that of petrolatum. In some embodiments the water-insoluble component and/or viscosity index improver is higher in MW, more branched, more flexible, stronger, tougher, higher melting, and/or more crystalline than blends of mineral oil combined with petrolatum.

Optional Non-Adhesive Self-Supporting Layer

The present denture adhesive compositions optionally comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Some embodiments may comprise non-adhesive cellulose derivatives, polyester, polypropylene, nylon, rayon, cloth, paper, microcrystalline wax, or mixtures thereof. Some embodiments may comprise polyester, polypropylene, rayon, nylon, cloth, and/or paper.

The non-adhesive self-supporting layer may be in any physical form suitable for providing strength and/or integrity to the present adhesive compositions. Such physical forms include non-woven, woven, continuous, chopped, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

Other Adhesive Components

The present invention compositions may also include other adhesive components. These adhesive components, if present, are used in a safe and effective adhesive amounts. In general, the other adhesive components may be present at a level of any combination of the ranges from about 0%, 10%, 20%, 30, or 40% to about 50%, 60%, 70%, 80%, or 90%, by weight of the composition.

Suitable adhesive components include a water-soluble hydrophilic colloid or polymer having the property of swelling upon exposure to moisture to form a mucilaginous mass. Such adhesive materials include natural gums, synthetic polymeric gums, AVE/MA copolymer acid, AVE/MA copolymer anhydride, AVE/MA/IB, synthetic polymers, mucoadhesive polymers, hydrophilic polymers, saccharide derivatives, other cellulose derivatives, and adhesive materials commonly employed in denture stabilizing compositions and compatible with the subject polymers of the present invention, and mixtures thereof. Examples of such materials include karaya gum, guar gum, gelatin, algin, sodium alginate, tragacanth, chitosan, polyethylene glycol, acrylamide polymers, carbopol, polyvinyl alcohol, polyamines, polyquartemary compounds, polybutenes, silicones, ethylene oxide polymers, polyvinylpyrrolidone, cationic polyacrylamide polymers.

In some embodiments, such materials may be other cellulose derivatives, polyethylene glycol, polyethylene oxide, karaya gum, sodium alginate, chitosan, polyvinyl alcohol, or mixtures thereof. In other embodiments, the materials may be other cellulose derivatives such as methylcellulose, hydroxyethylcellulose, hydroxypropylcellulose, hydroxypropylmethylcellulose, or mixtures thereof.

Other Ingredients

The present denture adhesive compositions which also comprise a non-adhesive self-supporting layer may also comprise a coating which is sticky to dry dentures and, if present, will be placed on one side of the denture adhesive composition. Compositions suitable for use as this type of adhesive layer include polybutenes, silicones, rubbers, petrolatum, natural polymers, synthetic polymers, and mixtures thereof. The adhesive layer may be present at a level of from about 0% to about 70%, in some embodiments from about 0.5% to about 20%, by weight of the composition.

Other suitable ingredients may include colorants, preservatives such as methyl and propyl parabens; thickeners such as silicon dioxide, and polyethylene glycol; and vehicles such as liquid petrolatum, petrolatum, mineral oil and glycerin. In some embodiments, polyethylene glycol, silicon dioxide, and/or petrolatum may be included. Colorants, preservatives, thickeners and vehicles may be present at levels of from about 0% to about 20%, by weight of the composition.

The compositions of the present invention may also include one or more components which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants.

The coolant can be any of a wide variety of materials. Included among such materials are carboxamides, menthol, ketals, diols, and mixtures thereof. In some embodiments, coolants in the present compositions may be the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional coolants may be selected from the group consisting of menthol, 3-1-menthoxypropane-1, 2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979. These agents may be present at a level of from about 0% to about 50%, by weight of the composition.

The present compositions may be used as a denture adhesive and/or used as a bioadhesive on wet tissue such as mucosal tissues, wounds, oral mucosa, etc. The present adhesive compositions can be used to deliver one or more therapeutic actives suitable for topical administration to mucosal or wet tissues. The phrase "therapeutic actives", as used herein, describes agents which are pharmacologically active when absorbed through wet tissue or mucosal surfaces of the body such as the oral cavity, wounds, or applied to the surfaces of the skin. Therapeutic actives may be present at a level of from about 0% to about 70%, by weight of the composition.

Therapeutic actives that are useful in the present compositions may include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, flavors, fragrances, or sensates (warming or cooling agents), and aldehyde derivatives such as benzaldehyde; insulin; steroids; and antineoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Process for Preparation of the Composition

A process for preparing denture adhesive compositions of the present invention (articles, creams, powders, wafers, liquids, aerosols, pastes) comprises conventional methods disclosed in the art. Conventional methods are taught in U.S. Pat. No. 5,525,652, issued Jun. 11, 1996, Clarke et al.; U.S. Pat. No. 3,003,988, issued Oct. 10, 1961, Germann et al.; U.S. Pat. No. 5,073,604, Holeva et al., issued Dec. 17, 1991; and U.S. Pat. No. 5,872,161, Liang et al., issued Feb. 16, 1999.

A process for the preparation of the present denture adhesive compositions optionally comprising a non-adhesive self-supporting layer, comprises coating a weighed amount of the adhesive components onto the non-adhesive self-supporting layer. This process is disclosed in U.S. Pat. No. 5,877,233, Liang et al, issued Mar. 2, 1999; U.S. Pat. No. 5,872,160, issued Feb. 16, 1999, Liang et al.; U.S. Pat. No. 5,880,172, Rajaiah et al., filed Oct. 25, 1996.

The term "mixture", as used in this "Process for Preparation the Composition" section, refers to a solution, slurry, or suspension.

The adhesive components may be coated on the non-adhesive self-supporting layer using various methods. These include: (a) wetting the non-adhesive self-supporting layer with water, uniformly sifting the adhesive component powder(s) onto the wet layer and then rewetting the layer with water; (b) dissolving the adhesive component(s) in water and/or other solvent(s) and coating the resulting mixture on the layer; (c) coating the layer with the mixture produced during AVE/MA polymer processing; (d) incorporating the adhesive component(s) into the layer as the layer is being formed; and (e) dissolving the adhesive component(s) in water and/or other solvent(s), wetting/coating the resulting mixture onto the layer, and uniformly sifting one or more adhesives in powder form onto the wet/coated layer and optionally re-coating/re-wetting the layer with the mixture and/or water; (f) the method of step (e) repeated multiple times; and (g) any combination of the methods in (a) through (f) above.

As disclosed above, the adhesive components may be dissolved in water and/or other solvents and the resulting mixture coated onto the layer.

When the adhesive compositions are prepared by dissolving the adhesive component(s) in water and/or other solvents, various embodiments of the process include: dissolving the polymers in one or more of the solvents for polymers; dissolving an optional adhesive in a suitable solvent and coating the resulting mixture onto the non-adhesive self-supporting layer and then optionally sifting one or more adhesives onto the coated layer. Coating the layer can be achieved by techniques commonly known in the art including extrusion, doctor blading, spraying, dipping, etc.

After the polymer has been deposited on the layer by one of the means described above, the layer is then dried. Next, the denture adhesive composition is mechanically softened by running it through a ring-roller or micro-cracker or any other suitable means. The composition is then pressed smooth in a hydraulic press or flat-roller or other suitable means. The composition is then die-cut into denture shapes. These shapes may facilitate application of the composition to the dentures.

The following examples further describe and demonstrate embodiments within the scope of the present invention. The examples are given solely for the purpose of illustration and are not to be construed as limitations of the present invention. Many variations of these are possible without departing from the spirit and scope of the invention.

EXAMPLE I

Salts of AVE/MA Copolymers A-J

| Component | A Grams | B Grams | C Grams | D Grams | E Grams |
|---|---|---|---|---|---|
| Water | 1876.38 | 1883.68 | 1888.88 | 1889.58 | 1898.62 |
| Calcium Hydroxide | | 11.39 | | 7.59 | 15.19 |
| Strontium Hydroxide | 43.62 | 24.93 | 24.93 | 18.7 | |
| Magnesium Oxide | | | 6.20 | 4.13 | 6.20 |
| AVE/MA Anhydride Polymer AN169 (from ISP) | 80.00 | 80.00 | 80.00 | 80.00 | 80.00 |
| Resulting Salt | Sr(70%) FA(30%) | Ca(30%) Sr(40%) FA(30%) | Mg(30%) Sr(40%) FA(30%) | Mg(20%) Ca(20%) Sr(30%) FA(30%) | Mg(30%) Ca(40%) (FA(30%) |

| Component | F Grams | G Grams | H Grams | I Grams | J Grams |
|---|---|---|---|---|---|
| Water | 1897.22 | 1896.27 | 1895.32 | 1894.37 | 1893.59 |
| Calcium Hydroxide | 22.78 | 23.73 | 24.68 | 25.63 | 25.55 |
| AVE/MA Anhydride Polymer (AN 169 from ISP) | 80.00 | 80.00 | 80.00 | 80.00 | 76.92 |
| Sodium Hydroxide (50% solution) | | | | | 3.94 |
| Resulting Salt | Ca(60) FA(40) | Ca(62.5) FA(37.5) | Ca(65)/ FA(35) | Ca(67.5) FA(32.5) | Ca (70) Na (5) FA (25) |

Compositions A to J exemplify salts of AVE/MA copolymers useful in the denture adhesive compositions of the present invention.

The components are weighed and added to a 4 liter reaction vessel while mixing. 15% the water is used to pre-slurry all powders except the AVE/MA. The residual powders are then washed down from the wall of the vessel. The mixture is then reacted at a temperature of from 80 to 95° C. The solution is then dried for about 16 to 24 hours in an oven at a temperature of from 65 to 75° C. All dried flakes are then milled to a fine powder.

Further as examples, the above salts may be modified by reacting the mixture with various levels NaOH between 0% and 10%, in addition to the ingredients listed above. Further as examples, the calcium in the above salts may be interchanged wholly or in part with magnesium and/or strontium. Further still as examples, the magnesium in the above salts can be interchanged wholly or in part with calcium and/or strontium and the strontium interchanged wholly or in part with magnesium and/or calcium.

EXAMPLE II

Salts of AVE/MA Copolymers M-O and R-U

| Component | M Grams | N Grams | O Grams | R Grams | S Grams | T Grams | U Grams |
|---|---|---|---|---|---|---|---|
| Water | 1897.28 | 1606.27 | 1605.30 | 1896.76 | 1897.28 | 1897.64 | 1897.99 |
| Calcium Hydroxide | 24.21 | 21.33 | 21.24 | 25.19 | 24.21 | 23.56 | 22.90 |
| Sodium Hydroxide | | | 1.35 | | | | |
| AVE/MA Anhydride Polymer AN169 BF | | | | 78.05 | 78.50 | 78.80 | 79.11 |
| AVE/MA Anhydride Polymer AN 169 | 78.50 | 66.10 | 65.81 | | | | |
| Resulting Salt | Ca (65) FA (35) | Ca (68) FA (32) | Ca (68) Na (2) FA (30) | Ca (68) FA (32) | Ca (65) FA (35) | Ca (63) FA (37) | Ca (61) FA (39) |

Compositions M-O and R-U exemplify salts of AVE/MA copolymers useful in the denture adhesive compositions of the present invention.

The components are weighed and added to a 4 liter reaction vessel while mixing. 15% the water is used to pre-slurry all powders except the AVE/MA. The residual powders are then washed down from the wall of the vessel. The mixture is then reacted at a temperature of from 80 to 95° C. The solution is then dried for about 16 to 24 hours in an oven at a temperature of from 65 to 75° C. All dried flakes are then milled to a fine powder.

Further as examples, the above salts may be modified by reacting the mixture with various levels of NaOH between 0% and 10%, in addition to the ingredients listed above. Further as examples, the calcium in the above salts may be interchanged wholly or in part with magnesium and/or strontium.

EXAMPLE III

Salts of AVE/MA Copolymers K-L and Comparative Examples P and Q

| Component | K (In Grams) | L (In Grams) | P (Comparative) (In Grams) | Q (Comparative) (In Grams) |
|---|---|---|---|---|
| Water | 1894.43 | 1896.41 | 1890.83 | 1892.77 |
| Calcium Hydroxide | 23.95 | 25.83 | 25.28 | 27.12 |
| Sodium Hydroxide (50% solution) | 3.98 | | 7.80 | 3.90 |
| AVE/MA Anhydride Polymer - AN169 (from ISP) | 77.65 | 77.76 | 76.09 | 76.20 |
| Resulting Salt | Ca (65) Na (5) FA (30) | Ca (70) Na (0) FA (30) | Ca (70) Na (10) FA (20) | Ca (75) Na (5) FA (20) |

Compositions K, and L exemplify salts of AVE/MA copolymers useful in the denture adhesive compositions of the present invention. Comparative examples P and Q exemplify salts of AVE/MA copolymers having free acid levels outside of the scope of the present invention.

The components are weighed and added to a 4 liter reaction vessel while mixing. 15% the water is used to pre-slurry all powders except the AVE/MA. The residual powders are then washed down from the wall of the vessel. The mixture is then heated in a heating mantle set at 88.5° C. and reacted for approximately two hours. The solution is then dried for approximately 22.5 hours in an oven at a temperature of 70° C. All dried flakes are then milled to a fine powder.

EXAMPLE IV

Evaluation of Denture Adhesive Compositions A1 and A2 and Comparative Compositions C1 and C2

TABLE 4

Denture Adhesive Compositions

| Composition | A1 Grams | A2 Grams | C1 Grams | C2 Grams |
|---|---|---|---|---|
| Salt K | 3.12 | | | |
| Salt L | | 3.12 | | |
| Salt P | | | 3.12 | |
| Salt Q | | | | 3.12 |
| Sodium Carboxymethylcellulose (High MW/Viscosity grade 7H3SX8F from Aqualon) | 1.88 | 1.88 | 1.88 | 1.88 |
| Total Cations | 70 | 70 | 80 | 80 |
| Free Acid | 30 | 30 | 20 | 20 |

TABLE 4A

Artificial Saliva Composition

| Ingredient | Amount per liter |
|---|---|
| K$_2$HPO$_4$ | 4.2 g |
| KH$_2$PO$_4$ | 3.2 g |
| KOH | 2 pellets (0.098 grams each) |
| Mineral Stock Solution | 5 ml |
| KCl | 8 g per 100 ml of Stock Solution |
| NaCl | 8 g |
| Na2SO4 | 0.264 g |
| MgCl2•6H2O | 0.7687 |

From the compositions listed in Table 4, five (5) grams of each of denture adhesive compositions A1 and A2 according to the present invention and comparative denture adhesive compositions C1 and C2 were made using example salts K, L, P and Q (listed above in Example III) and then assessed by an expert grader.

The denture adhesive compositions were formed according by the following procedures:

A powder blend composition was first formed by milling the AVE/MA salt flakes after tray drying, in a Fritsch mill with a 0.08 mm screen. The resulting milled composition was then placed in a vacuum oven pulling a 30 inches Hg vacuum for about 2 hours at 75° C. The AV/ME salt was then weighed and combined with the CMC in a glass vial. The powders were shake blended for about 30 seconds using a vortex mixer.

A hydrated sample composition was then formed by first weighing 0.5 grams of the powder blend into a plastic 14 ml polypropylene round-bottom tube vial (17×100 mm style). The vial was then placed on a VWR Analog vortex mixer and set on setting #10. The vial was positioned on the stirrer such that the powder swirls around inside the vial in a vortex form. 3.0 ml of the artificial saliva composition found in Table 4A was then added via a 10 ml syringe into the vortex formed by the powder in the tube (addition taking approximately one second). The mixing continued for an additional 3-5 seconds as the powder hydrated. The mixer was stopped and the resulting combination was immediately mixed further by hand with a metal spatula until all gel blocked particles were reduced to less than 1 mm in size and a uniform gel was formed. The cap was secured to the top of the vial and the cap-vial seal wrapped with Parafilm. The samples were then equilibrated in the vials for approximately 18 hours at about 23° C.

The compositions were then graded against each other by a professional grader using the following procedures and the results compiled in Table 4B.

The hydrated samples were removed from the vials using a metal spatula. The samples were manually stretched and pulled apart slowly until the breaking point. The broken pieces were pressed back together. The stretching/breaking/pressing back steps were repeated 4-8 times per sample to evaluate for the following properties:

Cohesion—assessed primarily by how much force is required to break the samples.

Tackiness—assessed by how sticky the sample is to fingers

Elastic—assessed by how much the samples spring back upon stretching and releasing or breaking.

Re-healing—assessed by how uniformly & easily the sample re-forms into a single mass similar to the original mass—with no seams, clumps, or segregated phases.

Mealiness—assessed by how clumpy, and non uniform the sample becomes after step-iv. In many instances this is also accompanied by "partially dry looking clumps".

Denture adhesives known to provide good hold and be consumer acceptable have medium-to-high cohesion, tackiness, and elasticity (the higher the better) and medium-to-low mealiness (the lower the better).

TABLE 4B

Results

| Composition | Level of Cations | Free Acid Levels | Grade |
|---|---|---|---|
| A1 | 70 | 30 | Medium cohesion, medium tackiness, medium elasticity, medium re-healing, and medium-to-low mealiness |
| A2 | 70 | 30 | Medium cohesion, medium-to-high tackiness, medium elasticity, medium re-healing, medium-to-low mealiness |
| C1 | 80 | 20 | Low cohesion, low tackiness, low elasticity, low re-healing, and high mealiness |
| C2 | 80 | 20 | Low cohesion, low tackiness, low elasticity, low re-healing, and high mealiness |

As can be seen in Table 4B, compositions A1 and A2 according to the present invention provide more desirable values of cohesion, tackiness, elasticity and mealiness versus comparative examples C1 and C2.

EXAMPLE V

Denture adhesive compositions in cream form can be made by blending together the following ingredients:

| | weight (grams) |
|---|---|
| White Mineral Oil | 89.74 |
| Petrolatum, White | 82.01 |
| Carboxymethylcellulose Sodium | 75.00 |

-continued

| | weight (grams) |
|---|---|
| Silicon Dioxide, Colloidal | 4.28 |
| Colorant (Opatint Red Dye) | 0.23 |
| An AVE/MA copolymer salt according to Example compositions A-O or R-U or mixtures thereof. | 123.75 |

The red dye, petrolatum, and mineral oil are weighed, heated and mixed in a glass jar at 50 to 60° C. until visually uniform. Then the powders (colloidal silicon dioxide, CMC, AVE/MA copolymer salt) are weighed and shake-blended together in a container. Thereafter, the powders are mixed into the liquid with a spatula until visually a uniform pink cream. The subject places the cream composition on the denture. Then the subject inserts the denture into his/her mouth and presses it into place. Such compositions would provide good hold and improved taste.

EXAMPLE VI

Denture adhesive compositions in powder form can be made by blending together the following ingredients:

| | weight (grams) |
|---|---|
| Carboxymethylcellulose Sodium | 39.00 |
| An AVE/MA copolymer salt according to Example compositions A-O or R-U or mixtures thereof. | 60.00 |
| Colloidal Silica | 1.00 |

All components are blended together. The above powder compositions can also be modified by using mixtures of the various AVE/MA salts. The subject places the composition on a pre-moistened denture, allowing it to hydrate briefly. Then the subject inserts the denture into his/her mouth and presses it into place.

EXAMPLE VII

Denture stabilizing compositions in wafer form can be made by wetting a 58" by 20" non-woven polyester (non-adhesive self-supporting layer) with water. Uniformly coat this wet sheet with the compositions listed below. Thereafter, rewet the layer with water. Dry the layer. Mechanically soften the composition by ring-roller, and then smooth the composition on a hydraulic press. Die-cut the composition into desired shapes. Moisten and apply these wafer compositions to the dentures. Then insert the denture into the mouth and press it into place.

| | weight (grams) |
|---|---|
| Carboxymethylcellulose Sodium | 60.00 |
| An AVE/MA copolymer salt according to Example compositions A-O or R-U or mixtures thereof. | 90.00 |

EXAMPLE VIII

Denture adhesive compositions in article or strip form can be made by blending together the following ingredients, extruding the resulting composition into sheets, and die-cutting to desired shapes.

| | weight (grams) |
|---|---|
| Carboxymethylcellulose Sodium | 75.00 |
| An AVE/MA copolymer salt according to Example compositions A-O or R-U or mixtures thereof. | 60.00 |
| Microcrystalline Wax | 135.00 |

The above compositions can also be modified by using mixtures of the various AVE/MA salts. The subject places the composition on a denture. Then the subject inserts the denture into his/her mouth and presses it into place.

EXAMPLE IX

Denture Adhesive Cream

| | Example | | | | | | |
|---|---|---|---|---|---|---|---|
| Ingredient | 9A % | 9B % | 9C % | 9D % | 9E % | 9F % | 9G % |
| Polymer Salt from Examples A-O or R-U or combination thereof | 33.00 | 28.75 | 28.75 | 28.75 | 28.75 | 24.00 | 33.00 |
| Sodium Carboxymethyl-cellulose | 20.00 | 24.25 | 24.25 | 24.25 | 24.25 | 29.00 | 20.00 |
| Mineral Oil, heavy white, USP (Kaydol) | 39.86 | 37.36 | 38.50 | 34.86 | 32.86 | 38.50 | 21.55 |
| Petrolatum, white | 0 | 0 | 0 | 0 | 0 | 0 | 19.72 |
| Colloidal Silicon Dioxide NF | 1.14 | 1.14 | 0.0 | 1.14 | 1.14 | 0.0 | 1.04 |
| Microcrystalline Wax W835 | 6 | 8.5 | 8.5 | 11 | 13 | 8.5 | 4.69 |

Procedure to make Example 9A-9B compositions: first connect a mixer with wall-scraper blades (Unimix from Haagen and Rinau) and hot water jacket to a water bath and a vacuum pump. Set the water bath of the hot water jacket to about 95° C. Add the mineral oil, petrolatum (where present) and/or microcrystalline wax to mixer vessel. Turn on the agitator to about 60 RPM; mix until their temperature reaches about 95° C. Add the "AVE/MA salt, carboxymethylcellulose, and silica via a funnel to the mixer with the vent open. Close the vent and stop mixing. Scrape off powder clumps. Re-start mixing at about 60 RPM. Pull about 24 inches Hg vacuum and mix until the batch reaches about 90° C. Reduce bath temperature to about 60° C. and continue mixing under vacuum until the batch reaches about 65° C. Stop mixing, turn off the pump, slowly open the vent, release the vacuum, and raise the lid. Fill the sample into a suitable container, such as a foil tube of about 1.4 oz in capacity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All percentages, parts and ratios are based upon the total weight of the compositions of the present invention, unless otherwise specified. All such weights as they pertain to listed ingredients are based upon the active level and, therefore, do not include solvents or by-products that may be included in commercially available materials, unless otherwise specified. The term "weight percent" may be denoted as "wt. %" herein. All molecular weights as used herein are weight average molecular weights unless otherwise specified.

Herein "comprising" means that other steps and other ingredients which do not affect the end result can be added. This term encompasses the terms "consisting of" and "consisting essentially of". The compositions and methods/processes of the present invention can therefore comprise, consist of, and consist essentially of the elements and limitations of the invention described herein, as well as any of the additional or optional ingredients, components, steps or limitations described herein.

The term "teeth" as used herein, refers to natural teeth as well as artificial teeth or dental prosthesis.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it will be obvious to those skilled in the art that various changes and modifications may be made without departing from the spirit and scope of the invention. It is therefore intended to cover in the appended claims all such changes and modifications that are within the scope of the invention.

What is claimed is:

1. A denture adhesive composition comprising a salt of a copolymer of alkyl vinyl ether-maleic acid or anhydride, wherein said adhesive composition comprises:
   a) from about 25% to about 45%, by weight of the composition, of a salt of a copolymer of alkyl vinyl ether-maleic acid or anhydride containing a cationic salt function comprising:
      i) from about 60% to about 72% cations selected from calcium, magnesium, or combinations thereof;
      ii) from 0% to about 10% sodium cations;
      iii) less than 1% zinc cations;
      iv) from about 25% to about 40% of a free acid component; and
      v) substantially free of strontium;
   b) from about 10% to about 30%, by weight of the composition of a carboxymethyl cellulose; and
   c) a carrier
   wherein the carrier is at least one of natural wax, synthetic wax, petrolatum, polyvinyl acetate, natural oils, synthetic oils, fats, silicone, dimethicone, silicone resins, hydrocarbons, essential oils, caprilic/capric triglycerides, polybutene, oleic acid, or stearic acid.
   wherein the natural oil comprises mineral oil; and
   wherein the natural oil further comprises at least one of oleic acid or stearic acid.

2. The denture adhesive composition according to claim 1, wherein the cationic salt function is substantially free of zinc cations.

3. The denture adhesive composition according to claim 2, wherein the cationic salt function comprises calcium cations and from about 25% to about 35% free acid component.

4. The denture adhesive composition according to claim 1, wherein the cationic salt function comprises from about 65% to about 70% calcium cations, from about 0% to about 5% sodium cations and from about 25% to about 35% free acid component.

5. The denture adhesive composition according to claim 1, wherein the denture adhesive composition comprises from about 20% to about 30% sodium carboxymethylcellulose by weight of the composition.

6. The denture adhesive composition according to claim 1, further comprising one or more ingredients selected from the group consisting of additional adhesive components, plasticizers, colorants, preservatives, thickeners, vehicles, flavors, fragrances, sensates, and mixtures thereof.

7. The denture adhesive composition according to claim 1, wherein the denture adhesive composition is a cream.

8. A denture adhesive composition comprising a salt of a copolymer of alkyl vinyl ether-maleic acid or anhydride, wherein said adhesive composition comprises:
   a) from about 25% to about 45%, by weight of the composition, of a salt of a copolymer of alkyl vinyl ether-maleic acid or anhydride containing a cationic salt function comprising:
      i) from about 60% to about 72% cations selected from calcium, magnesium, or combinations thereof;
      ii) from 0% to about 10% sodium cations;
      iii) less than 1% zinc cations;
      iv) from about 25% to about 40% of a free acid component; and
      v) substantially free of strontium;
   b) from about 10% to about 30%, by weight of the composition of a carboxymethyl cellulose; and
   c) a carrier
   wherein the carrier is at least one of natural wax, synthetic wax, petrolatum, polyvinyl acetate, natural oils, synthetic oils, fats, silicone, dimethicone, silicone resins, hydrocarbons, essential oils, caprilic/capric triglycerides, polybutene, oleic acid, or stearic acid;
   wherein the denture adhesive composition comprises at least one non-adhesive self-supporting layer.

9. A denture adhesive composition comprising a salt of a copolymer of alkyl vinyl ether-maleic acid or anhydride, wherein said adhesive composition comprises:
   a) from about 25% to about 45%, by weight of the composition, of a salt of a copolymer of alkyl vinyl ether-maleic acid or anhydride containing a cationic salt function comprising:
      i) from about 60% to about 72% cations selected from calcium, magnesium, or combinations thereof;
      ii) from 0% to about 10% sodium cations;
      iii) less than 1% zinc cations;
      iv) from about 25% to about 40% of a free acid component; and
      v) substantially free of strontium;
   b) from about 10% to about 30%, by weight of the composition of a carboxymethyl cellulose; and
   c) a carrier
   wherein the carrier comprises microcrystalline wax.

10. The denture adhesive composition according to claim 1, wherein the denture adhesive composition is substantially free of magnesium.

11. The denture adhesive composition according to claim 1, wherein the denture adhesive composition is substantially free of sodium.

12. The denture adhesive composition according to claim 1, wherein the cationic salt function comprises about 70% calcium cations, about 5% sodium cations and about 25% free acid component.

13. The denture adhesive composition according to claim 1, wherein the cationic salt function comprises about 65% calcium cations, about 0% sodium cations and about 35% free acid component.

14. A method of improving the adhesion of dentures to the oral cavity by applying the denture adhesive composition of claim 1 to dentures, the oral cavity, or both, and thereafter securing the denture to the ridge or palate of the oral cavity.

15. A denture adhesive composition comprising a salt of a copolymer of alkyl vinyl ether-maleic acid or anhydride, wherein said adhesive composition comprises:
   a) from about 25% to about 45%, by weight of the composition, of a salt of a copolymer of alkyl vinyl ether-maleic acid or anhydride containing a cationic salt function comprising:
      i) from about 60% to about 70% calcium cations;
      ii) from 0% to about 5% sodium cations;
      iii) substantially free of zinc cations;
      iv) from about 25% to about 35% of a free acid component; and
      v) substantially free of strontium;
   b) from about 10% to about 30%, by weight of the composition, of a carboxymethyl cellulose having a molecular weight of from about 500,000 to about 900,000; and
   c) a carrier;
   wherein the carrier is at least one of natural wax, synthetic wax, petrolatum, polyvinyl acetate, natural oils, synthetic oils, fats, silicone, dimethicone, silicone resins, hydrocarbons, essential oils, caprilic/capric triglycerides, polybutene, oleic acid, or stearic acid;
   wherein the natural oil comprises mineral oil; and
   wherein the natural oil further comprises at least one of oleic acid or stearic acid.

16. The denture adhesive composition according to claim 15, wherein the denture adhesive composition is a cream.

* * * * *